(12) United States Patent
Essenreiter et al.

(10) Patent No.: US 7,922,391 B2
(45) Date of Patent: Apr. 12, 2011

(54) DETERMINING CALIBRATION INFORMATION FOR AN X-RAY APPARATUS

(75) Inventors: Robert Essenreiter, München (DE); Michael Bertram, Markt Schwaben (DE); Martin Ringholz, Erlangen (DE)

(73) Assignee: Brainlab AG, Feldkirchen (DE)

( * ) Notice: Subject to any disclaimer, the term of this patent is extended or adjusted under 35 U.S.C. 154(b) by 0 days.

(21) Appl. No.: 12/436,267

(22) Filed: May 6, 2009

(65) Prior Publication Data

US 2009/0285366 A1 Nov. 19, 2009

Related U.S. Application Data

(60) Provisional application No. 61/054,187, filed on May 19, 2008.

(30) Foreign Application Priority Data

May 15, 2008 (EP) ..................................... 08156293

(51) Int. Cl.
*G01D 18/00* (2006.01)
(52) U.S. Cl. ....................................... 378/207; 378/205
(58) Field of Classification Search .................. 378/207, 378/205
See application file for complete search history.

(56) References Cited

U.S. PATENT DOCUMENTS

| 4,791,934 | A | 12/1988 | Brunnett |
| 6,484,049 | B1* | 11/2002 | Seeley et al. .................. 600/426 |
| 6,865,253 | B2* | 3/2005 | Blumhofer et al. ............. 378/65 |
| 2002/0188194 | A1* | 12/2002 | Cosman ........................ 600/426 |

FOREIGN PATENT DOCUMENTS

| DE | 199 36 408 A1 | 3/2001 |
| DE | 199 63 440 A1 | 7/2001 |
| DE | 102 15 808 | 11/2003 |
| DE | 10 2005 059 301 A1 | 6/2006 |
| EP | 1 313 065 | 5/2003 |

OTHER PUBLICATIONS

Office Action corresponding to European Patent Application No. 08156293 dated Feb. 4, 2009.

* cited by examiner

*Primary Examiner* — Hoon Song
(74) *Attorney, Agent, or Firm* — Renner, Otto, Boisselle & Sklar, LLP

(57) ABSTRACT

A device and method are provided that enable calibration information to be determined for an x-ray apparatus that performs a three-dimensional x-ray scan. The calibration information is determined using an adapting method, wherein the adapting method is based on a position of an x-ray source relative to an x-ray unit marker device during image acquisition, an x-ray unit data set that describes the position of the x-ray unit marker device during image acquisition, and a two-dimensional calibration data set that describes at least one and preferably two actual two-dimensional x-ray images produced by irradiating a calibration object.

15 Claims, 3 Drawing Sheets

DETERMINING CALIBRATION INFORMATION FOR AN X-RAY APPARATUS

RELATED APPLICATION DATA

This application claims the priority of U.S. Provisional Application No. 61/054,187, filed on May 19, 2008, which is hereby incorporated in its entirety by reference.

FIELD OF THE INVENTION

The present invention relates to determining calibration information for an x-ray apparatus which can in particular be used in the medical field, in particular in image-guided surgery (IGS).

BACKGROUND OF THE INVENTION

U.S. Pat. No. 4,791,934 discloses a system for stereotactic surgery, in which computer tomography is used. Two-dimensional images are derived from three-dimensional data, in order to guide the position of a surgical instrument on the basis of them.

Reference is also made to DE 102 15 808 B4.

SUMMARY OF THE INVENTION

It is an object of the invention to determine calibration information for an x-ray apparatus which performs a three-dimensional x-ray scan.

The above object is solved by the subjects of the independent claims.

Advantageous developments follow from the dependent claims.

"Pointers" are pointing devices provided with markers which can be detected by means of the camera of a navigation system, so as to determine the position of the pointer, in particular the tip of the pointer. In this way, it is possible to read the position of points, in particular landmarks in an anatomical structure, into the navigation system.

One advantage of the invention is that the time-consuming process of reading data in by means of pointers is avoided. Another advantage of the invention is that a calibration object (at least the edges of which can be identified in a (two-dimensional and three-dimensional) x-ray image) does not have to be provided with markers which can be identified both optically (by a detection device of a navigation system) and in the x-ray image. The calibration object can therefore be designed in a cost-effective way. It is not necessary to precisely shape the calibration object, at least in accordance with a preferred variant of the invention; rather, the shape and/or dimensions of the calibration object can be arbitrary and in particular, in accordance with the preferred variant of the invention, unknown. The method in accordance with the invention nonetheless allows calibration information to be determined which includes information on the positional relationship and/or spatial relationship between the x-ray apparatus reference frame and the three-dimensional scan reference frame and which is in particular required for navigating and is in particular determined with the aid of the navigation system. The calibration information preferably includes information which can be represented by a transformation. This transformation is referred to here as the calibration transformation. The calibration transformation includes in particular a transformation between the x-ray apparatus reference frame and the three-dimensional scan reference frame. The calibration information can be able to be represented by mathematical functions, images or variables, such as for example a set of vectors which represents the spatial relationship between the x-ray apparatus reference frame and the three-dimensional scan reference frame.

In the following example description, the calibration transformation is cited as an example of calibration information.

In the method in accordance with the invention, a three-dimensional calibration data set is preferably provided. The three-dimensional calibration data set is produced by a three-dimensional scan of a calibration object by means of x-ray beams. The raw data thus ascertained is preferably processed using a data processing device which calculates, from the raw data, a three-dimensional calibration model which three-dimensionally represents the calibration object. This calibration model is preferably described in a reference frame of the three-dimensional scan. The calibration model lies in this three-dimensional scan reference frame, wherein an x-ray unit (for example, a C-arm) is for example moved in the three-dimensional scan reference frame during the scanning process, in particular following a predefined movement trajectory. This provides a three-dimensional scanning path along which the x-ray unit is moved during the scanning process, in order to capture the calibration object from different directions. The recordings thus produced from different directions represent raw data which is then processed to form the calibration model, as described above. A portion of the three-dimensional scanning path, for example the start position of the x-ray unit which it assumes at the beginning of the three-dimensional scan, lies in a reference frame which is referred to here as the x-ray apparatus reference frame.

The calibration transformation includes and in particular describes a transformation between the x-ray apparatus reference frame and the three-dimensional scan reference frame, wherein "include" means that it can also be represented by a product and/or progression of a transformation between the x-ray apparatus reference frame and the three-dimensional scan reference frame and another transformation. The other transformation is for example a transformation between another reference frame (for example a navigation reference frame, in particular a reference frame of the camera of the navigation system or a reference frame of the operating theatre, or a reference frame of a detected marker device), which is not the three-dimensional scan reference frame, and the x-ray apparatus reference frame and/or a transformation between the three-dimensional scan reference frame and said other reference frame.

The calibration transformation described here can be used, as described below, to determine the relative position between an object and an anatomical model. In this respect, it is possible to proceed in such a way that the position of the object is transformed into the three-dimensional scan reference frame using the calibration transformation. This is the preferred variant which is discussed in more detail below. It is of course also possible to proceed in such a way that a three-dimensional anatomical model is transformed, using the calibration transformation, into a reference frame in which the object lies. This also results in the relative position between the object and the anatomical model. In the following, the calibration transformation is described such that it includes a transformation from the x-ray apparatus reference frame into the three-dimensional scan reference frame (the first transformation direction). In accordance with the invention, however, the scenario is also to be included which relates to the aforementioned second variant, according to which the calibration transformation describes a transformation from the three-dimensional scan reference frame to the x-ray apparatus reference frame (the second transformation direction). In general terms, the calibration transformation in accordance with the invention thus includes a transformation between the x-ray apparatus reference frame and the three-dimensional scan reference frame, wherein both transformation directions are intended to be covered by the term "calibration transformation". In the following example description, it is assumed, purely by way of example, that the term "calibration transformation" relates to the first (and preferred) transformation direction from the x-ray apparatus reference frame to the three-dimensional scan reference frame, unless this is explicitly described otherwise.

Data is also preferably provided which describe the recording conditions of two-dimensional x-ray images in more detail. In particular, x-ray source relative position data is provided which contains information on the x-ray beam imaging geometry, and which in particular allow the position of an x-ray source to be calculated relative to an x-ray unit marker device and/or which in particular allow the course of the x-ray beams through the calibration object to be determined relative to the position of the x-ray unit marker device. The calculated position of the x-ray source is defined as the calculated point of intersection of the x-ray beams which are detected. This position can, but need not, match the actual position of the x-ray beam source. The position of the x-ray source follows mathematically if x-ray images are evaluated, on the basis of the principles of pinhole camera imaging.

Marker devices preferably include passive or active markers, the position of which with respect to each other is determined, or which are in a known and predefined position relative to each other. The passive markers reflect beams or waves, for example infrared beams or ultrasound waves, whereas the active markers emit the same. The reflected or emitted beams or waves are detected by the detection device (of the navigation system), for example a camera which in particular comprises two detection modules. The position of the marker device can be determined from the detection signals. This is used in particular in the IGS mentioned above.

The method in accordance with the invention is preferably also provided with a so-called two-dimensional calibration data set. The two-dimensional calibration data set describes at least one two-dimensional x-ray image, preferably two or more x-ray images. The data of a single two-dimensional x-ray image is sufficient (in accordance with a first variant) as a constituent of the two-dimensional calibration data set, if the calibration object has known dimensions and/or contours and/or distances between elements, such that it is possible to calculate, from the imaged dimensions, contours or elements and their distances, where the calibration object was situated when it was recorded. Since the x-ray beams diffuse from the x-ray source in the shape of a beam cone, the imaged calibration object appears larger on the x-ray image, the further away the calibration object is from the x-ray source. Since the x-ray beam imaging geometry is known from the x-ray source relative position data, it is possible to deduce the distance between the calibration object and the x-ray source from the size of the imaged calibration object (or parts of the calibration object). An inclination (for example, relative to the centre beam path from the x-ray source to the x-ray detector) can be determined from the change in shape (for example, a square part imaged in the shape of a rhombus). The centre beam path generates the image point in the centre of the x-ray image. Its course is preferably known from the x-ray source relative position data. This additional information (size and/or change in shape) can be used in such a way that it is even possible to omit a second x-ray image for determining the calibration transformation. In the following, however, the second variant comprising (at least) two two-dimensional x-ray images is described by way of example, as a preferred variant. A higher level of accuracy is in particular expected in this second variant. The two variants can of course be combined, in particular in order to further increase the level of accuracy.

The two-dimensional x-ray images are thus preferably produced under the aforesaid (at least two) different recording conditions, which are preferably designed such that the x-ray beam cones in the respective recordings irradiate the registration object from different directions. Preferably, an angle of approximately 90° exists between the directions; the preferred angle is for example between 60° and 120°. Thus, the x-ray source assumes different relative positions relative to the calibration object under different recording conditions.

As mentioned above, x-ray source relative position data is provided, from which the position of the x-ray unit marker device relative to the x-ray source follows. The relative position between the x-ray source and the x-ray unit marker device is at least approximately constant, but can change for the different recording conditions, for example due to a deformation of the C-arm. This can be taken into account by the x-ray source relative position data for the different recording conditions including different data which contains information from which it is possible to determine the respective, possibly slightly different x-ray beam imaging geometry, in particular the relative position between the x-ray unit marker device and the x-ray source. The x-ray source relative position data is preferably determined from the two-dimensional x-ray images by evaluating them. An x-ray source determining aid is preferably used in this respect which is situated in the beam path during the recording of at least one of the two-dimensional x-ray images (of the calibration object) and/or in a separately recorded two-dimensional x-ray image and which has a known position relative to the x-ray unit marker device. In accordance with an alternative and simpler embodiment, the relative position between the x-ray source and the x-ray unit marker device is known. In particular, it may be assumed that particular prior-known relative positions are given for particular recording conditions, such that an x-ray source determining aid is not required. Preferably, however, the aforementioned x-ray source determining aid is used, in particular in order to achieve a higher level of accuracy. It is in particular possible to take into account that the relative positions can change in the course of the service life of an x-ray apparatus.

The x-ray source determining aid preferably includes structures or elements which are spaced apart from each other to a known extent in the direction of the x-ray beam course and which can be detected in the x-ray image. The x-ray beam imaging geometry can be determined from the distances between the elements and/or contours of the x-ray source determining aid which can be determined from the image (x-ray image). In particular, by back-projecting the imaged elements and/or contours via the known position of the elements and/or contours of the x-ray source determining aid, it is possible to determine a centre of projection which corresponds to the position of the x-ray source. The position of the x-ray source is therefore determined. The position of the x-ray source is in particular described via the position of the centre of projection (x-ray source) relative to the x-ray unit marker device. The different positions of the x-ray source which result for the different recording conditions are in particular described in the x-ray apparatus reference frame (in which for example the start position of the x-ray unit lies).

For determining the centre of projection and therefore the position of the x-ray source from the x-ray images, mathematical methods are preferably used which are based on the principles of a pinhole camera. In this respect, reference is made to the following publications, which are also incorporated into the disclosure by reference:

1. "An Efficient and Accurate Camera Calibration Technique for 3D Machine Vision", Roger Y. Tsai, Proceedings of IEEE Conference on Computer Vision and Pattern Recognition, Miami Beach, Fla., 1986, pages 364-374.
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344. See also http://www.cs.cmu.edu/~rgw/TsaiDesc.html
3. Publication by Ziv Yaniv, "Fluoroscopic X-ray Image Processing and Registration for Computer-Aided Orthopedic Surgery".

The same start positions and/or end positions are preferably used when passing through a three-dimensional scanning path for determining the position of the calibration model and for determining the position of an anatomical model, as is described below.

The x-ray unit marker device can for example be attached to an x-ray beam detector or to an (actual) x-ray beam source of the x-ray apparatus. The x-ray beam detector can be moved together with the x-ray beam source, in order to realize the different recording conditions (recording directions).

An x-ray unit data set is preferably provided which respectively describes the position of the x-ray unit marker device for the different recording conditions. This position can for example be described in a reference frame which is used when calculating the calibration transformation, such as for example the x-ray apparatus reference frame or the patient reference frame mentioned below. It could also for example be described in a navigation reference frame. The x-ray unit data set thus provides the method in accordance with the invention with information on the position of the x-ray unit marker device (in particular on its relative position under the different recording conditions) when the two-dimensional x-ray images (of the calibration object) are produced. This position is for example described in the x-ray apparatus reference frame.

The method is then provided with information on the relative position between the x-ray unit marker device and the x-ray source for the different recording conditions when producing the two-dimensional x-ray images. The position of the x-ray unit marker device for the respective recording conditions is also known. It is thus possible to calculate the respective position of the x-ray source for the different recording conditions relative to each other, preferably in the x-ray apparatus reference frame but for example also in the navigation reference frame, from the x-ray source relative position data and the x-ray unit data set.

The method is thus provided with information on the recording conditions, in particular the position of the x-ray source when producing the two-dimensional x-ray images. By means of an adapting method, in particular a mathematical and/or numerical adapting method, it is then possible to ascertain how the calibration object would have to lie in a reference frame, preferably in the x-ray apparatus reference frame (but also for example in the navigation reference frame) in order to generate the two-dimensional x-ray images. In this respect, it is in particular possible to adduce the calibration model and for example virtually displace it, in particular translate and/or rotate it, in the x-ray apparatus reference frame (or in the navigation reference frame) by means of a test transformation, until the two-dimensional x-ray images result when the calibration model is virtually irradiated with the x-ray beams from the x-ray source. When determining the valid test transformation in this way, the x-ray source respectively assumes the different positions in order to virtually generate the different x-ray images, wherein the (virtual) x-ray source respectively has one of the previously determined positions, for example in the x-ray apparatus reference frame or in the navigation reference frame, ascertained for the respective recording of the actual two-dimensional x-ray images. If the calibration transformation includes the transformation direction from the x-ray apparatus reference frame to the three-dimensional scan reference frame (the first transformation direction), then the calibration transformation is the inverse of the test transformation. If the alternative variant of the calibration transformation as described above is chosen, in which the calibration transformation includes the direction from the three-dimensional scan reference frame to the x-ray apparatus reference frame (the second transformation direction), then the valid test transformation corresponds to the calibration transformation. Overall, the position of the calibration model can thus be transformed using the calibration transformation, such that an optimum adaptation is achieved. In particular, it is possible by means of the valid test transformation to transform the position of the calibration model in the three-dimensional scan reference frame into the position of the calibration model in the x-ray apparatus reference frame for which, when the calibration model is virtually irradiated (in the x-ray apparatus reference frame), virtual two-dimensional x-ray images result which are optimally adapted to the actual two-dimensional x-ray images.

Whether an adaptation has been achieved to the desired extent, and the calibration transformation thus determined to the desired level of accuracy, can for example be determined from the extent to which the virtual x-ray images match the actual x-ray images. In this respect, the position of prominent regions, for example edges or corners, of the calibration model in the virtual x-ray image can for example be compared with the position of the corresponding edges or corners in the actual x-ray image. By means of a least square fit method, for example, it is possible to optimize a variable which represents the extent of the match. Predetermined ranges for this extent can be predefined. If the match is within the predefined range, then the match can be regarded as desirable and the calibration transformation thus determined can thus be accepted as having been determined.

If it is assumed that the position of the calibration model is varied with the aid of the test transformations in order to determine the calibration transformation, for example by varying a rotational and/or translational component, then test positions of the calibration model are generated by the test transformations. A set of virtual x-ray images which result for the predefined positions of the x-ray source are then preferably generated for the respective test position. In the aforesaid verification of the match, the virtual x-ray images thus generated are compared with the actual x-ray images, so as to determine a value for the match from the entirety of the images. If the match is given to a predetermined extent, then the test transformation is found to be valid and the calibration transformation is determined from it.

As mentioned, the two-dimensional calibration data set preferably circumscribes not only at least one two-dimensional x-ray image of the calibration object but also an image of the x-ray source determining aid which is irradiated by the x-ray beam cone and forms a pattern in the two-dimensional x-ray image. Thus, when generating the two-dimensional x-ray images, the x-ray beams irradiate not only the calibration object but preferably also the x-ray source determining aid. The x-ray source determining aid can for example be grid-shaped, wherein the grid is designed to absorb x-ray beams. Preferably, at least two grids are arranged at a predetermined distance, wherein the grids are transverse to the diffusion direction of the x-ray beams. It is also for example possible to embed elements which are impermeable to x-ray beams, such as for example cylinders or spheres (x-ray markers) in a material which is permeable to x-ray beams, wherein said elements in turn leave behind patterns in the two-dimensional x-ray image and are preferably also at least spaced apart in the diffusion direction of the x-ray beams such that they can be detected in the x-ray image. The pattern can be regular or irregular. Geometric variables of the pattern, in particular distances between prominent elements of the pattern (for example, of the grid), are preferably known. The position of the x-ray sources, in particular the centre of projection (of the x-ray source), is preferably calculated—using the principles of the pinhole camera already mentioned above—on the basis of the known distances between prominent pattern elements (for example, grid intersections) and on the basis of the two-dimensional x-ray images. Distortions and/or imaging errors, caused in particular by the cushion-shaped surface of the fluorescent screen in the image converter of the x-ray receiver, can also be corrected in the two-dimensional x-ray images, in order to then ultimately determine a calibration model which is as free of imaging errors and distortions as possible with the aid of the (rectified) two-dimensional calibration data set. The prominent pattern elements can in particular be used in the adapting method for determining the calibration transformation, by virtually irradiating a virtual x-ray source determining aid which is situated in the same position as the actual x-ray source determining aid and has the same dimensions. In particular, the virtual two-dimensional x-ray images can thus be calculated in such a way as if the x-ray source were irradiating not only the calibration model but also the x-ray source determining aid which is situated in a known position and generates an image pattern in the x-ray image. As already mentioned, geometric data of the x-ray source determining aid, which for example describes distances between prominent elements of the x-ray source determining aid or the size and dimensions of prominent elements such as for example marker spheres, is preferably known. A rectified calibration model can be calculated with the aid of the geometric data of the x-ray source determining aid. The calibration model can also be scaled on the basis of them, if the x-ray apparatus is not already outputting sufficiently accurately scaled data.

In accordance with one embodiment, a three-dimensional measurement data set is preferably provided which describes a three-dimensional anatomical model of an anatomical structure of a patient in a patient reference frame, wherein said structure is captured by a three-dimensional x-ray scan (three-dimensional measurement x-ray scan). The calibration transformation determined can be used to determine the position of an object relative to the position of the three-dimensional anatomical model. Accordingly, a calibration transformation which has been determined in accordance with the above method can be used in order for example to determine the position of an object, for example an instrument or implant, relative to an anatomical structure during an operation, without requiring additional steps such as for example capturing the anatomical structure with a pointer or recording two-dimensional x-ray images.

The x-ray apparatus reference frame is preferably used in the method described above for determining the position of the object relative to the position of the three-dimensional anatomical model, since it may be assumed that the position of the three-dimensional scan reference frame has not changed relative to the x-ray apparatus reference frame since the calibration transformation was ascertained. If, for example, the navigation reference frame is used, then a change in the position of the x-ray apparatus may have occurred since the calibration transformation was determined. A change in the position of the x-ray apparatus would mean a change in the position of the three-dimensional scanning path. The three-dimensional scanning path during the capture of the calibration object would thus have a different position to the three-dimensional scanning path during the capture of the anatomical structure. In other words, the x-ray apparatus reference frame thus changes its position in the navigation reference frame. In order to take this into account, scanning path relative position data is in this case in particular preferably provided which describes a change in the position of the three-dimensional scanning path in the navigation reference frame which has occurred between the three-dimensional calibration x-ray scan and the three-dimensional measurement x-ray scan. Such a change in position can for example be captured by comparing the position of the x-ray unit marker device at the same placement of the x-ray unit (for example, the start position of the scanning process) within the three-dimensional scanning path. A marker device, which preferably does not change position during the x-ray scan, can also be additionally attached to the x-ray apparatus. By determining the position of this marker device during the three-dimensional calibration x-ray scan and during the three-dimensional measurement x-ray scan, it is possible to capture the change in the position of the three-dimensional scanning path. This change in position is preferably described by a transformation (the "navi-scan" transformation) which for example includes rotational and/or translational elements. This "navi-scan" transformation thus describes the change in the position of the x-ray apparatus reference frame in the navigation reference frame. If this transformation is combined with the transformation between the x-ray apparatus reference frame and the three-dimensional scan reference frame (the "x-ray scan" transformation), this also results in an example of the calibration transformation. This example is a transformation between the navigation reference frame and the three-dimensional scan reference frame and includes, as discussed above, the transformation from the x-ray apparatus reference frame to the three-dimensional scan reference frame (the "x-ray scan" transformation). Both the navi-scan transformation and the x-ray scan transformation are examples of a calibration transformation.

One possible navigation reference frame is for example a reference frame in which the operating theatre lies or in which a detection device (for example, a camera) of the navigation system lies. The position which an object, for example a part of a body or an instrument, assumes in the navigation reference frame can be converted by means of the navi-scan transformation into the position which the object assumes in the three-dimensional scan reference frame. The position which an object assumes in the x-ray apparatus reference frame can be converted by means of the x-ray scan transformation into the position which the object assumes in the three-dimensional scan reference frame.

The three-dimensional measurement data set describes the position of the three-dimensional anatomical model in the three-dimensional scan reference frame. If, as described above, the position of the object is likewise calculated in the three-dimensional scan reference frame with the aid of the calibration transformation, then the position of the object relative to the three-dimensional anatomical model is obtained, i.e. for example the position of an instrument relative to the three-dimensional anatomical model, for example a body structure such as the femur, wherein this can be used for IGS.

In practice, it will often occur that the anatomical structure changes its position, in particular its position in the x-ray apparatus reference frame and/or navigation reference frame, after the three-dimensional measurement data set has been generated. In order to nonetheless be able to calculate the current position of an object, for example an instrument, relative to the three-dimensional anatomical model in accordance with the current situation, object data is preferably provided. The object data preferably includes object/x-ray unit data and/or object/patient data. The object/x-ray unit data describes the position of the object in the x-ray apparatus reference frame, i.e. for example relative to the x-ray unit marker device. The object/patient data describes the position of an object in a patient reference frame, i.e. for example relative to a patient marker device which is connected, spatially fixed, to the anatomical structure. Using the object/patient data has the advantage over using the object/x-ray unit data that when determining the position of the object relative to the three-dimensional anatomical model, it is also possible to completely remove the x-ray apparatus, i.e. the x-ray unit marker device no longer has to be detectable. If it is still detectable, then the relative position between the object and the x-ray unit marker device can be determined at any time, so as to update the object/x-ray unit data. Thus, if the position of the object in the x-ray apparatus reference frame is known from the object/x-ray unit data, then the position of the object relative to the three-dimensional anatomical model can be determined by applying the calibration transformation. In the following, the embodiment in which the position of the object relative to the three-dimensional anatomical model is determined on the basis of the object/patient data is described in more detail.

The patient marker device is for example a reference star which is fastened to the anatomical structure of the patient, such as for example a bone of the patient. Since the object is preferably likewise provided with a marker device, it is thus possible for the navigation system to determine the relative position between the object and the patient marker device and thus the object/patient data mentioned. Marker relative position data is preferably also provided which describes the position of the patient marker device relative to the x-ray unit marker device or relative to another marker device which lies in the x-ray apparatus reference frame. The relative position can be described in the x-ray apparatus reference frame (or in another reference frame, for example the navigation reference frame). A measurement transformation is preferably calculated on the basis of the marker relative position data. The measurement transformation in particular describes a transformation from the patient reference frame, in which the patient marker device lies, to the x-ray apparatus reference frame. Thus, if the measurement transformation is applied to the position of an object which is in particular described in the patient reference frame, then the position of the object is in particular obtained in the x-ray apparatus reference frame. If the calibration transformation (more specifically, the x-ray scan transformation) is then applied to this, then the position of the object in the three-dimensional scan reference frame results. This position is independent of a relative movement of the anatomical structure relative to the x-ray apparatus, since the object/patient data is described in the reference frame of the patient marker device. Thus, the measurement transformation is preferably combined with the calibration transformation, and the combined transformation (also referred to as the registration transformation) allows the position of the object relative to the three-dimensional anatomical model to be determined, even if the anatomical structure (and thus the assigned anatomical model) moves relative to the x-ray apparatus after the three-dimensional measurement data set has been produced.

The three-dimensional calibration data set preferably describes a calibration object which in particular exhibits an irregular shape which shows contours in two-dimensional x-ray images. One advantage of this is that, as opposed to a regular contour such as for example a cube or cylinder, there are no symmetry properties of the registration object, which make it difficult or impossible to clearly determine the recording direction. Asymmetrical registration objects, in particular registration objects with no plane of symmetry, axis of symmetry or point of symmetry, are therefore preferred.

The present invention also relates to a program which, when it is run on a computer or loaded onto a computer, causes the computer to perform the method described above, in particular to process the data in the way described above.

The aforesaid program can in particular be stored on a data storage medium such as for example a CD, DVD, ROM memory cards, etc. The program can also be transmitted via a digital signal wave, for example as a download. The aforesaid program is thus in particular embodied by a data storage medium or a signal wave.

The invention is also directed to a data processing device, in particular a computer, which includes the aforesaid program, i.e. on which the program has been loaded or is running.

The invention is also directed to a navigation system such as is for example used for image-guided navigation in operations. The navigation system preferably includes the aforesaid data processing device and additionally a detection device which is capable of detecting marker devices. It is in particular suitable for detecting the marker devices which are used to generate the data which is provided to the aforesaid method and/or which is processed by the aforesaid program. In particular, the x-ray unit marker device is detected by the detection device, and the detection signals are fed to the data processing device. The detection device preferably also detects the patient marker device and/or another marker device attached to the x-ray apparatus, and in particular a marker device which is attached to an object (for example, an instrument).

The navigation system is preferably combined with or includes an x-ray apparatus which includes the x-ray unit which is used to generate the three-dimensional calibration data set, the two-dimensional calibration data set and in particular the three-dimensional measurement data set. The x-ray unit is preferably connected to the data processing device for relaying the captured x-ray signals, so as to generate the aforesaid data sets, in order to ultimately be able to provide them to the program or method.

In the following detailed description, other advantages and features of the invention are disclosed, wherein different features of different embodiments can be combined with each other.

DETAILED DESCRIPTION

Figure 1:
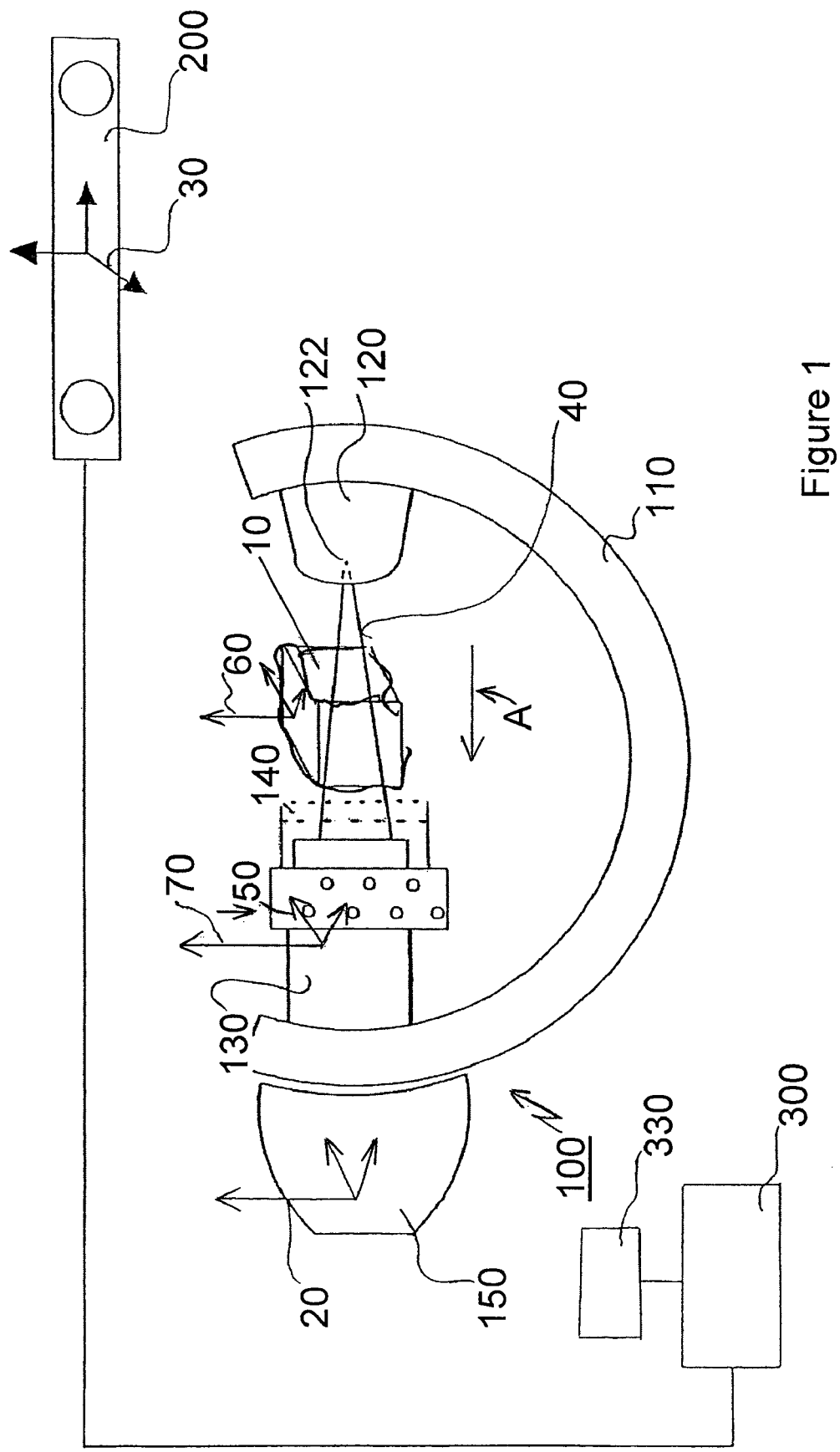
FIG. 1 shows an embodiment of the navigation system in accordance with the invention, with the x-ray unit in its horizontal position.

FIG. 1 shows a design in accordance with the invention. An x-ray apparatus 100, more specifically a C-arm x-ray apparatus 100, consists of a resting part 150 which is not moved relative to a camera 200 of a navigation system during a three-dimensional scan. The x-ray apparatus 100 also includes a movable x-ray unit 110 comprising an x-ray beam source 120 and an x-ray light detector 130. A so-called registration kit 50 is attached to the x-ray light detector 130 and serves as an x-ray unit marker device. A cone-shaped x-ray beam 40 is emitted from a point 122 which represents an x-ray source 122 which is defined by the fact that straight lines which represent the x-ray beams 40 intersect in the point 122. The x-ray beams are captured by the x-ray light detector 130. An x-ray grid 140 which serves as an x-ray source determining aid is irradiated by the x-ray beam cone 40 in such a way that the x-ray grid 140 is visually captured by the x-ray light detector 130. The pattern of the x-ray grid 140 can thus be identified in the recording captured by the x-ray light detector. The x-ray grid 140 preferably includes two grids which are spaced apart from each other to a known extent in the diffusion direction of the x-ray beams (for example, in the direction of the centre axis of the x-ray beam cone). The spatial relationship between the x-ray grid 140 and the kit 50 is known. The relative spatial relationship between the kit 50 and the grids of the x-ray grid 140 is in particular also known. It is possible to determine how the x-ray beams have diffused in the recording from the known distance relationships between the two (or more) grids of the x-ray grid 140 and/or between marker elements of the x-ray grid which are in particular spaced apart from each other in the diffusion direction of the x-ray beams, and by evaluating the distance relationships between the grid elements or marker elements in the two-dimensional x-ray image. The position of the x-ray source 122, in particular relative to the kit 50, can thus be determined by projection, in particular by applying pinhole camera principles.

Figure 2:
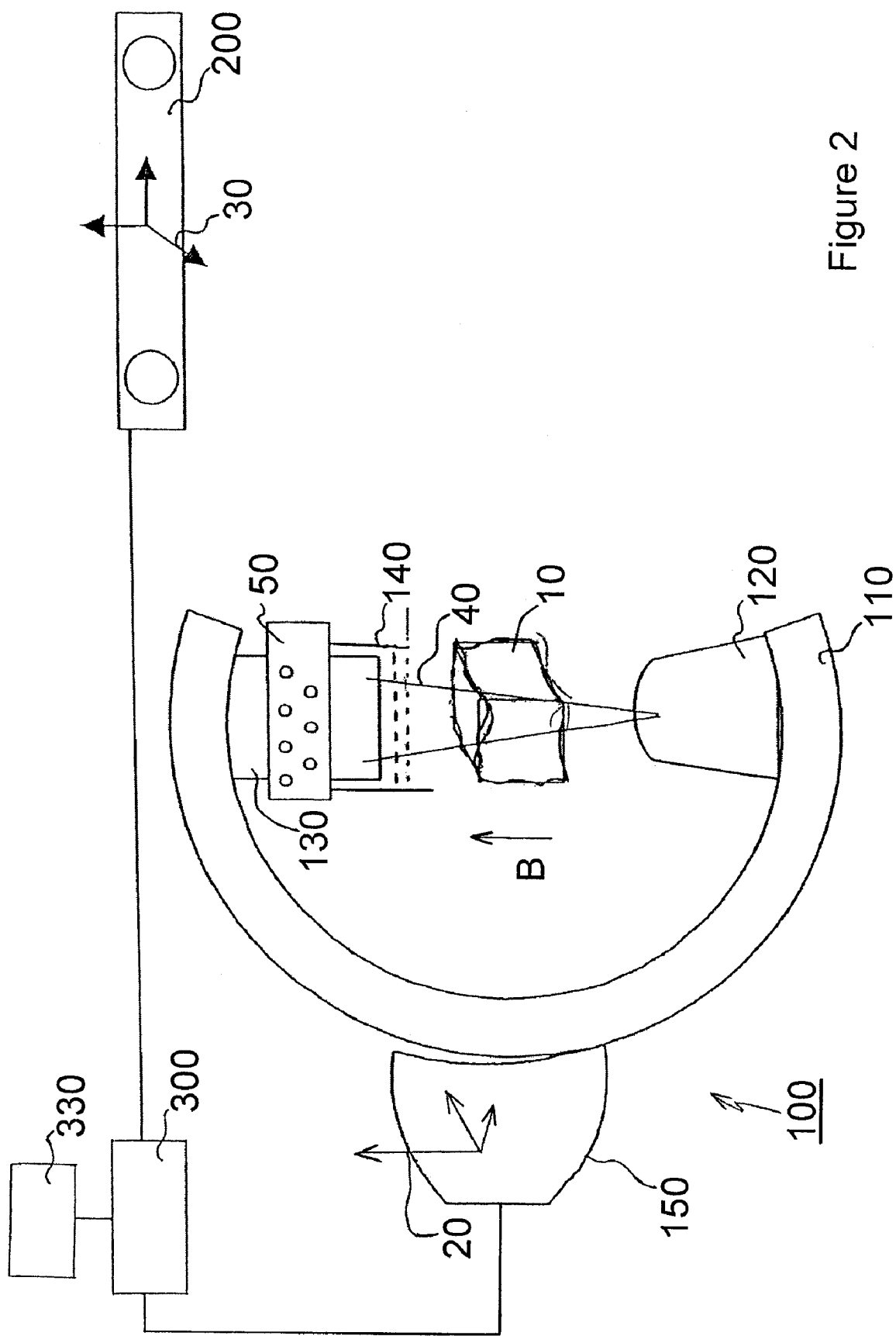
FIG. 2 shows the embodiment of FIG. 1, with the x-ray unit in its vertical position.

A marker device is preferably likewise attached to an instrument 500 (see FIG. 3) and detected by the detection device of the navigation system. If the transformations which are required in order to represent the position of the instrument 500 in the three-dimensional scan reference frame are described, then the following situation results:

$M_{70-60}$: this matrix describes a calibration transformation from the x-ray apparatus reference frame 70, in which for example the kit 50 lies in its start position, to the three-dimensional scan reference frame 60. This calibration transformation has been determined in accordance with the method described above. Two two-dimensional images of the calibration object 10 have for instance been produced in the placements shown in FIG. 1 and FIG. 2, and a three-dimensional scan of the calibration object 10 has been taken. In the two-dimensional x-ray images, which have been respectively produced as shown in FIGS. 1 and 2, the recording is preferably taken with the x-ray grid 140. The two-dimensional and three-dimensional data thus obtained is processed in the way already described above, in order to be able to determine the positional relationship between the three-dimensional scan reference frame 60 and the x-ray apparatus reference frame 70. The calibration transformation, more specifically the x-ray scan transformation, is thus ultimately determined.

$M_{80-60}$: this matrix describes a so-called registration transformation from the patient reference frame 80, in which the reference star 420 lies (see FIG. 3), to the three-dimensional scan reference frame 60.

$M_{80-70}$: this matrix describes a measurement transformation from the patient reference frame 80, in which the reference star 420 lies, to the x-ray apparatus reference frame 70.

The registration matrix $M_{80-60}$ is calculated as follows:

$$M_{80-60}=M_{70-60}*M_{80-70}$$

i.e. it is obtained by multiplying the matrices $M_{70-60}$ by $M_{80-70}$.

If an instrument 500 comprising a reference star 520 is then observed by the camera 200 of the navigation system, then the position of the instrument 500 in the reference frame 80 of the reference star 420 (i.e. the object/patient data) can be calculated. The calculation is made on the basis of the detected position of the reference star 520 and on the basis of the known relative position between the reference star 520 and the instrument 500 or a part of the instrument such as for example the tip of the instrument, and on the basis of the detected position of the reference star 420.

Preferably, the position of the instrument 500 relative to the three-dimensional anatomical model of the anatomical structure 410 is calculated on the basis of the method in accordance with the invention. In this respect, a vector $V_{80}$ which for example represents the calculated position of the tip of the instrument 500 in the patient reference frame 80 (of the reference star 420) can for example be multiplied by the aforementioned matrix $M_{80-60}$ as follows:

$$V_{60}=M_{80-60}*V_{80}.$$

The resultant vector $V_{60}$ then describes the position of the tip of the instrument in the three-dimensional scan reference frame 60. The position of the three-dimensional model of the anatomical structure in the three-dimensional scan reference frame is also known, from the three-dimensional measurement data set. It is thus possible to determine how the tip of the instrument 500 lies relative to the three-dimensional model of the anatomical structure. This relative position can in particular be displayed in real time on a screen 330 of the navigation system. This relative position is also not affected by a movement of the x-ray apparatus relative to the anatomical structure, such that the instrument 500 can be navigated relative to the anatomical model without further x-ray recordings.

In order to determine the position of the x-ray source, more specifically the centre of projection of the beams, relative to the kit 50, the x-ray grid 140 preferably includes a number of elements (x-ray markers), for example spheres, on preferably at least two planes. Preferably, at least six spheres are known on at least two planes, i.e. the position of these spheres relative to the kit 50 and thus in the reference frame 70 is preferably known. By applying the pinhole camera principle known from the prior art, it is possible to determine the position of a centre of projection from this known position of the marker spheres and/or from the distances between the marker spheres and from the relative position and/or distances between the imaged marker spheres which can be gathered from the two-dimensional x-ray images. Reference is made in this respect to the literature already mentioned above.

The direction in which the recording is taken is indicated by A and an arrow in FIG. 1. The direction points from the x-ray source to the x-ray light detector and lies in the horizontal in the example shown. The calibration object 10 is shown in FIG. 1 such that it has an approximately cubic shape. Preferably, however, it is irregularly shaped. A model of a human spinal column may for example be taken as the calibration object. Preferably, however, the calibration object does not have the shape of a basic geometric solid such as for example a cube, cuboid, cylinder, sphere or pyramid, but is rather asymmetrically shaped (with no plane, axes or points of symmetry).

Firstly, the calibration object 10 is for example captured by a three-dimensional scan, as indicated by FIGS. 1 and 2, wherein FIG. 1 for example shows the beginning of the three-dimensional scanning process, wherein the x-ray beam cone runs horizontally (0° placement), whence it rotates approximately about an axis which passes through the imaginary centre point of the circular C-arm. The rotation passes for example through the placement shown in FIG. 2, in which the x-ray beam cone 40 runs vertically (90° placement) up to a placement (not shown) which for example represents a 150° to 180° rotation with respect to the placement shown in FIG. 1. The direction of the x-ray recording is indicated by B and an arrow. The captured image data is fed to a data processing device which produces from it the three-dimensional calibration data set which three-dimensionally represents the calibration object. The calibration model is represented in the three-dimensional scan reference frame 60.

The three-dimensional scan is preferably taken without the x-ray grid 140. The three-dimensional calibration data set and thus the calibration model is calculated on the basis of the scan data. Two two-dimensional x-ray images of the calibration object are preferably captured in addition to the three-dimensional scan (i.e. before or after the three-dimensional scan), wherein the calibration object 10 preferably does not change its position, i.e. its has the same position as during the three-dimensional x-ray scan. The two two-dimensional x-ray images are preferably fluoroscopic images. The two-dimensional x-ray images are preferably taken with the x-ray grid 140 mounted. They form the basis for the two-dimensional calibration data set. A so-called image intensifier, which is part of the C-arm, is preferably also used in order to increase the sensitivity of the x-ray light detector. The two two-dimensional x-ray images are preferably taken from different directions relative to the registration object. The directions are preferably oblique and in particular perpendicular, as in the example shown in FIGS. 1 and 2. The two two-dimensional x-ray images can thus for example be taken from the direction A and the direction B.

Once the two two-dimensional images and the three-dimensional scan of the calibration object have been captured, an adapting method (matching method) is performed in order to determine how the calibration model, which two-dimensionally represents the calibration object, would have to lie between the x-ray beam source 120 and the x-ray beam detector 130 in order to generate the two two-dimensional images. How such an adapting method is performed has already been described above. Reference is also made to U.S. Pat. No. 4,791,934.

In the adapting method, it is thus possible to generate virtual two-dimensional images from the calibration model. The position of the calibration model relative to the x-ray source is varied, for example by means of a translational and/or rotational transformation which serves as a test transformation. Preferably, two virtual two-dimensional x-ray images are produced which are generated using two x-ray sources which have the relative spatial position such as was provided when the two actual two-dimensional x-ray images are recorded. The relative positional relationship of the directions A and B and/or the x-ray source can in particular be determined from the relative positional relationship of the kit 50 in the two recordings (FIG. 1 and FIG. 2), as captured by the camera 200. By accepting the relative positional relationship for the adapting process as having been predefined, the adapting process for determining the registration transformation can be performed more quickly.

As already discussed, the use of the x-ray grid in particular allows the x-ray source, i.e. in particular the position of the x-ray source (centre of projection of the x-ray beams), to be determined. It can also be used for scaling the calibration model. The calibration transformation in accordance with the invention can thus not only describe a positional relationship between the calibration model in the three-dimensional scan reference frame 60 and the calibration model in the x-ray apparatus reference frame 70 or navigation reference frame 30, but additionally allows in particular a verification of the scaling such as is output by the x-ray apparatus and/or a new scaling which can for example be expressed by an enlargement or reduction and/or rectification of the calibration model. The kit 50 lies in the x-ray apparatus reference frame 70 in the start position of the scanning process shown in FIG. 1. The calibration model lies in the three-dimensional scan reference frame 60.

The calibration process described above is preferably performed before an operation. The calibration transformation thus determined is stored and can then be used for registering an instrument 500 relative to an anatomical model of an anatomical structure of a patient.

Figure 3:
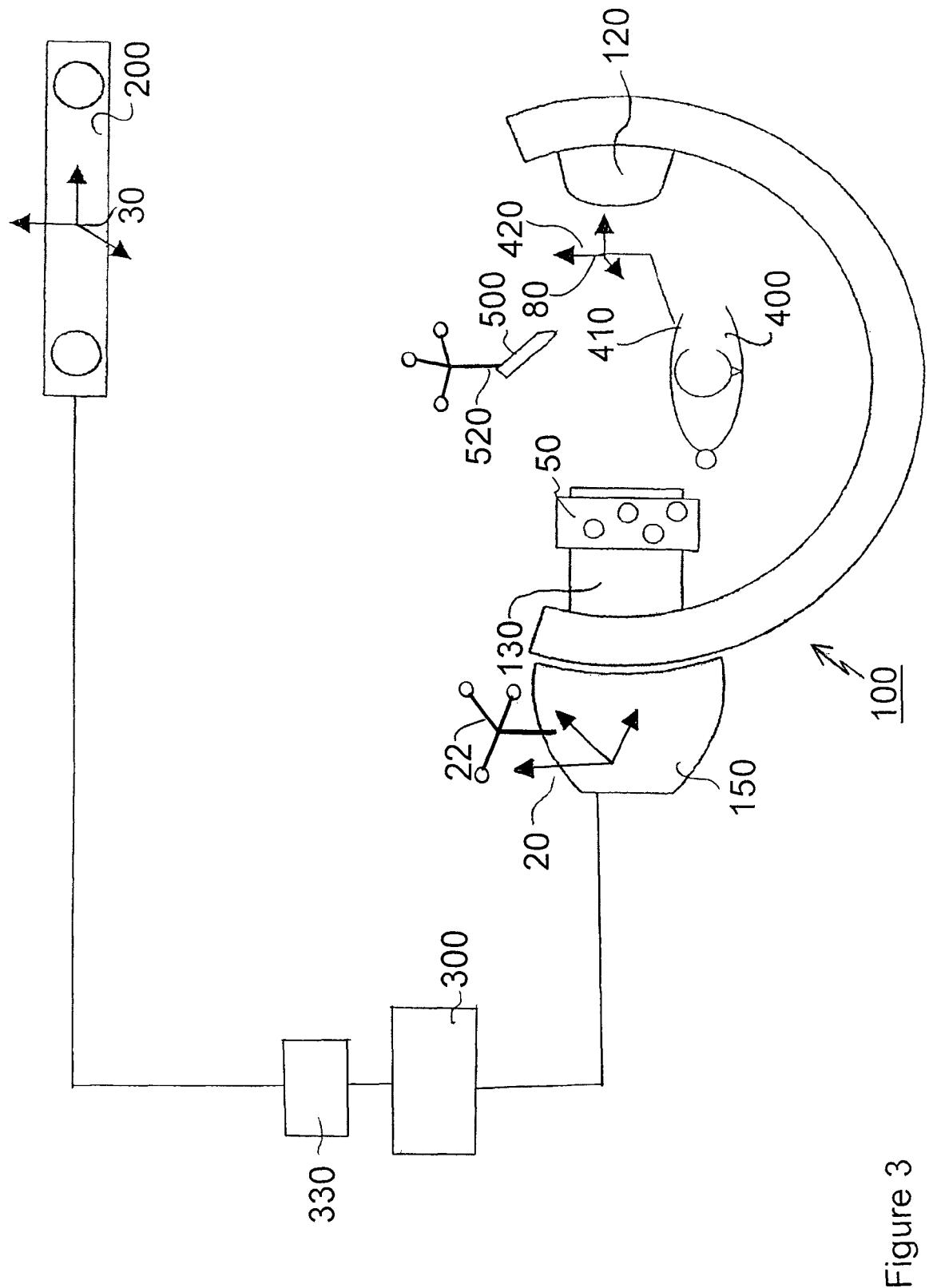
FIG. 3 shows the embodiment of FIG. 1, with a patient.

FIG. 3 shows a patient 400 lying in the x-ray apparatus 100. A three-dimensional x-ray scan is taken of an anatomical structure 410 of the patient 400. A reference star 420 is attached to the anatomical structure 410 of the patient and includes markers, in particular passive markers. The passive markers reflect light, in particular infrared radiation emitted by an infrared emitter (not shown). The markers can also be designed to be active, such that they emit light. The markers are detected by the camera 200 of the navigation system. The camera 200 also detects markers which are attached to kit 50, so as to identify the position of the kit 50.

By detecting the kit 50 when the position of the x-ray unit 110, 120, 130 (for example, the start position) or a reference star 22 attached to the part 150 is known, it is possible to determine whether the position of the x-ray apparatus 100 has changed relative to the camera 200, as compared to the calibration process described above in connection with FIGS. 1 and 2. It is in particular possible to determine whether the position of the x-ray apparatus reference frame 70, i.e. for example the position of the kit 50 in the scanning start position or the position of the reference frame 20, has changed. Since the reference frame 20 lies in the reference frame 70, the reference frame 20 can also be regarded as an example of an x-ray apparatus reference frame. It is also possible to determine whether the position of the scanning path along which the x-ray source 120 and the x-ray beam detector 130 are moved during the three-dimensional scan has changed relative to the camera 200. In this way, it is possible to determine a transformation which describes the change in the position of the x-ray apparatus reference frame 70 or also the scanning path.

If it is assumed that a three-dimensional x-ray scan (three-dimensional measurement x-ray scan) of the anatomical structure 410 has been taken, then it is possible to mathematically, in particular numerically, generate a three-dimensional anatomical model of the anatomical structure 410, as has been analogously achieved when determining the calibration model from the three-dimensional calibration x-ray scan. This anatomical model is provided in the three-dimensional scan reference frame 60 of the x-ray apparatus.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method for determining calibration information which includes information on a spatial relationship between an x-ray apparatus reference frame and a three-dimensional scan reference frame, comprising:
    obtaining a three-dimensional calibration data set representing a three-dimensional calibration model of a calibration object in the three-dimensional scan reference frame, wherein the calibration model is determined from scan data generated by a three-dimensional calibration x-ray scan of the calibration object, wherein during the three-dimensional calibration x-ray scan an x-ray unit is moved along a three-dimensional scanning path relative to the calibration object, and at least a portion of the three-dimensional scanning path lies in the x-ray apparatus reference frame;
    obtaining x-ray source relative position data that includes information on the position of an x-ray source of the x-ray unit relative to an x-ray unit marker device attached to the x-ray unit when actual two-dimensional x-ray images are produced;
    obtaining a two-dimensional calibration data set that describes a first of the actual two-dimensional x-ray images produced by irradiating at least the calibration object in a first position of the x-ray source in the x-ray apparatus reference frame, and which also describes at least one of:
    a) a second of the actual two-dimensional x-ray images produced by irradiating at least the calibration object, which is spatially fixed as compared to the first two-dimensional x-ray image, in a second position of the x-ray source in the x-ray apparatus reference frame different from the first position; or
    b) the dimensions of the calibration object;
    obtaining an x-ray unit data set that describes the position of the x-ray unit marker device when the at least one actual two-dimensional x-ray image is generated; and
    determining the calibration information using an adapting method based on the x-ray source relative position data, the x-ray unit data set and the two-dimensional calibration data set, said calibration information including information on the spatial relationship between the x-ray apparatus reference frame and the three-dimensional scan reference frame.

2. The method according to claim 1, further comprising using the determined calibration information for image-guided navigation.

3. The method according to claim 1, wherein the adapting method adapts at least one virtual two-dimensional x-ray image of the calibration model to at least one of the actual two-dimensional x-ray images.

4. The method according to claim 1, further comprising determining a virtual two-dimensional x-ray image by virtually irradiating the calibration model with virtual x-ray beams emitted from a virtual x-ray source situated in the first position, wherein the calibration information includes a calibration transformation that is determined in such a way that the position of the calibration model is transformed by the calibration transformation, such that the adaptation results for the transformed position, and/or wherein in order to ascertain the virtual two-dimensional x-ray images, the calibration model is virtually irradiated by x-ray beams of a virtual x-ray source which assumes the same positions as the positions of the actual x-ray source when the actual two-dimensional x-ray images are generated.

5. The method according to claim 4, wherein the calibration transformation is determined based on a valid transformation, the valid test transformation found by changing a test transformation until a match between the virtual and actual x-ray images is achieved to a predetermined extent by means of the test transformation, wherein the test transformation thus determined is the valid transformation.

6. The method according to claim 5, wherein the test transformation includes a rotational and a translational component, wherein the components are changed in order to determine the calibration transformation.

7. The method according to claim 1, wherein the x-ray source relative position data is obtained from the at least one actual two-dimensional x-ray image generated by irradiating an x-ray source determining aid with x-ray beams from the x-ray source, and from the x-ray source relative position data.

8. The method according to claim 1, further comprising obtaining a three-dimensional measurement data set that describes a three-dimensional anatomical model of an anatomical structure, the three-dimensional measurement data set captured by a three-dimensional measurement x-ray scan in the three-dimensional scan reference frame.

9. The method according to claim 8, further comprising:
obtaining object/x-ray unit data that describes the position of an object in the x-ray apparatus reference frame; and
determining the position of the object relative to the three-dimensional anatomical model based on the object/x-ray unit data and the calibration transformation.

10. The method according to claim 8, further comprising:
obtaining object/patient data that describes the position of an object in a patient reference frame, wherein a patient marker device is present in the patient reference frame and is connected, spatially fixed, to the anatomical structure;
obtaining marker relative position data that describes the position of the patient marker device in the x-ray apparatus reference frame;
determining a measurement transformation based on the marker relative position data;
determining the position of the object relative to the three-dimensional anatomical model based on the object/patient data, the measurement transformation and the calibration transformation.

11. The method according to claim 1, wherein the three-dimensional calibration data set describes an irregularly shaped calibration object which shows contours in two-dimensional x-ray images.

12. A non-transitory computer-readable storage medium with an executable program stored thereon, wherein the program instructs a processor to perform the steps of claim 1.

13. A data processing device for determining the position of a calibration object, which is subject to a three-dimensional x-ray scan, in a navigation reference frame, the data processing device comprising:
logic that obtains a three-dimensional calibration data set representing a three-dimensional calibration model of the calibration object in the navigation reference frame, wherein the calibration model is determined from scan data generated by a three-dimensional calibration x-ray scan of the calibration object, wherein during the three-dimensional calibration x-ray scan an x-ray unit is moved along a three-dimensional scanning path relative to the calibration object, and at least a portion of the three-dimensional scanning path lies in the x-ray apparatus reference frame;
logic that obtains x-ray source relative position data that includes information on the position of an x-ray source of the x-ray unit relative to an x-ray unit marker device attached to the x-ray unit when two-dimensional x-ray images are produced;
logic that obtains a two-dimensional calibration data set that describes a first of the actual two-dimensional x-ray images produced by irradiating at least the calibration object in a first position of the x-ray source in the x-ray apparatus reference frame, and which also describes at least one of:
a) a second of the actual two-dimensional x-ray images produced by irradiating at least the calibration object, which is spatially fixed as compared to the first two-dimensional x-ray image, in a second position of the x-ray source in the x-ray apparatus reference frame different from the first position; or
b) the dimensions of the calibration object;
logic that obtains an x-ray unit data set that describes the position of the x-ray unit marker device when the at least one actual two-dimensional x-ray image is generated; and
logic that determines the position of the object based on calibration information obtained using an adapting method, said adapting method using the x-ray source relative position data, the x-ray unit data set and the two-dimensional calibration data set, said calibration information including information on the spatial relationship between the x-ray apparatus reference frame and the three-dimensional scan reference frame.

14. A navigation system, comprising:
the data processing device according to claim 13; and
a detection device for detecting the x-ray unit marker device and for providing marker detection signals to the data processing device.

15. The navigation system according to claim 13, comprising: an x-ray apparatus for providing x-ray beam detection signals to the data processing device, wherein the x-ray apparatus includes an x-ray beam detection device.

* * * * *